(12) United States Patent
Bjørn et al.

(10) Patent No.: US 8,841,252 B2
(45) Date of Patent: Sep. 23, 2014

(54) PHARMACEUTICAL FORMULATION

(75) Inventors: Søren Bjørn, Lyngby (DK); Hans Holmegaard Sørensen, Virum (DK); Peter Langballe, Charlottenlund (DK); Silke Møller Larsen, Charlottenlund (DK); Kristen Ebbehøj, Nærum (DK); Birthe Lykkegaard Hansen, Værløse (DK)

(73) Assignee: Novo Nordisk Health Care AG, Zurich (CH)

( * ) Notice: Subject to any disclaimer, the term of this patent is extended or adjusted under 35 U.S.C. 154(b) by 247 days.

(21) Appl. No.: 12/575,886

(22) Filed: Oct. 8, 2009

(65) Prior Publication Data

US 2010/0029569 A1 Feb. 4, 2010

Related U.S. Application Data

(63) Continuation of application No. 11/734,823, filed on Apr. 13, 2007, now abandoned, which is a continuation of application No. 10/349,480, filed on Jan. 22, 2003, now abandoned, which is a continuation of application No. 08/842,293, filed on Apr. 23, 1997, now abandoned.

(60) Provisional application No. 60/028,620, filed on Aug. 28, 1996.

(30) Foreign Application Priority Data

Apr. 24, 1996 (DK) ........................................ 0490/96

(51) Int. Cl.
*A61K 38/27* (2006.01)
*A61P 5/06* (2006.01)
*A61P 3/04* (2006.01)

(52) U.S. Cl.
USPC ........................... 514/11.4; 514/5.1; 530/399

(58) Field of Classification Search
None
See application file for complete search history.

(56) References Cited

U.S. PATENT DOCUMENTS

| | | | |
|---|---|---|---|
| 4,816,568 A | 3/1989 | Hamilton, Jr. et al. | |
| 4,917,685 A | 4/1990 | Viswanathan et al. | |
| 5,023,088 A | 6/1991 | Wong et al. | |
| 5,045,312 A | 9/1991 | Aston et al. | |
| 5,096,885 A | 3/1992 | Pearlman et al. | |
| 5,126,324 A | 6/1992 | Clark et al. | |
| 5,401,829 A | 3/1995 | James et al. | |
| 5,552,385 A | 9/1996 | Christensen et al. | |
| 5,763,394 A * | 6/1998 | O'Connor et al. | 514/12 |
| 5,849,700 A | 12/1998 | Sørensen et al. | |
| 5,849,704 A | 12/1998 | Sørensen et al. | |
| 6,013,773 A * | 1/2000 | Kobayashi et al. | 530/399 |
| 6,448,225 B2 | 9/2002 | O'Connor et al. | |
| 7,048,938 B2 | 5/2006 | Patel et al. | |
| 2006/0029635 A1 | 2/2006 | Slebold et al. | |

FOREIGN PATENT DOCUMENTS

| | | |
|---|---|---|
| AU | 30771/89 | 9/1989 |
| EP | 0 303 746 A1 | 2/1989 |
| EP | 0 374 120 A2 | 2/1989 |
| EP | 0374120 | 6/1990 |
| HU | 9410832 | 12/1992 |
| JP | 7-502516 | 3/1995 |
| JP | 7-509719 | 10/1995 |
| WO | WO 89/09614 | 10/1989 |
| WO | WO 93/12811 | 7/1993 |
| WO | WO 93/12812 | 7/1993 |
| WO | WO 93/19776 | 10/1993 |
| WO | WO 94/03198 | 2/1994 |
| WO | WO 95/35116 | 12/1995 |
| WO | WO 96/11702 | 4/1996 |
| WO | WO 96/11704 | 4/1996 |
| WO | WO 96/21459 | 7/1996 |
| WO | WO 96/21460 | 7/1996 |

OTHER PUBLICATIONS

Dasamido Derivative of Biosynthetic Human Growth Hormone; Biotechnology and Applied Biochemistry, vol. 10, pp. 326-337 (1998).
Daugherty, Ann L. et al—Inter. Jour. of Pharmaceutics—vol. 45—1998—pp. 197-206.
Becker et al., Biotechnology and Applied Biochemistry, vol. 10, pp. 326-337 (1998).
Fong H. K. et al. ;"Hormone and Factors that Stimulate Growth of a Rat Islet Tumor Cell Line in Serum-Free Medium", Diabetes (1981); vol. 30; pp. 1022-1028.
Cotes et al.; "Dose Regimens of Human Growth Hormone: Effects of Continuous Infusion and of a Gelatin Vehicle on Growth in Rats and Rate of Absorption in Rabbits"; J. Endocrinology (1980); vol. 87; pp. 303-312.
Health Reference Nutrition Library [online], retrieved from the internet on Feb. 17, 2005 http://www.chwframe.staywellsolutionsonline.com/modules/HealthLib/HydrolyzedCollagen.asp.
FibroGen; http://www.fibrogen.com/gelatin/ [online]; retrieved from the internet on Feb. 17, 2005.
Yu-Chang et al., J. Parent Sci. & Tech., vol. 42, pp. S3-S26 (1988).
Manning et al., Pharmaceutical Research, vol. 6, No. 11, pp. 903-918 (1989).
Johnson et al., The Journal of Biological Chemistry, vol. 264, No. 24, pp. 14262-14271 (1989).
Teh et al., Journal of Biol. Chem., vol. 262, No. 14, pp. 6472-6477 (1987).
Becker et al., Biotech. and App. Biochem., vol. 10, pp. 326-337 (1988).
Wang et al., J. of Parenteral Science and Technology, vol. 42, p. S3-S27 (1988).

(Continued)

*Primary Examiner* — Michael Borin
(74) *Attorney, Agent, or Firm* — Rosemarie R. Wilk-Orescan

(57) ABSTRACT

The invention relates to aqueous pharmaceutical formulations comprising human growth hormone, histidine, poloxamer, phenol, and mannitol.

2 Claims, No Drawings

(56) References Cited

OTHER PUBLICATIONS

Jensen et al., Biotech. and Bioengineering, vol. 36, No. 1, p. 1-11 (1990).
Gellerfors et al., Acta PFdiatr Scan [Suppl], vol. 370, pp. 93-100 (1990).
Kaufman, Pharmaceutical Research, vol. 7, No. 3, pp. 289-292 (1990).
Riggen et al., Analytical Biochem., vol. 167, pp. 199-209 (1987).
Becker et al., Biotech, and Applied Biochem., vol. 9, pp. 478-487 (1987).
Arthur Osol ed., Mack Publishing Co., Easton, PA, Remington's Pharmaceutical Science, 16$^{th}$ ed., p. 1535 (1980).
Houghten et al., Arch. of Biochem. Biophysics, vol. 178, pp. 350-355 (1977).

* cited by examiner

PHARMACEUTICAL FORMULATION

CROSS-REFERENCE TO RELATED APPLICATIONS

This application is a continuation of U.S. application Ser. No. 11/734,823, filed on Apr. 13, 2007, which is a continuation of U.S. application Ser. No. 10/349,480, filed on Jan. 22, 2003 (published as US-2003-0162711-A1), which is a continuation of U.S. application Ser. No. 08/842,293, filed on Apr. 23, 1997, and claims priority under 35 U.S.C. 119 of Danish application no. 0490/96 filed on Apr. 24, 1996, and U.S. provisional application No. 60/028,620, filed on Aug. 28, 1996, the contents of which are fully incorporated herein by reference.

FIELD OF THE INVENTION

The invention relates to novel pharmaceutical formulations comprising growth hormone, or a derivative of growth hormone, and an amino acid selected from the group of Asp, Ile, Val, Leu, or His, or a derivative of histidine, or a peptide comprising at least one basic amino acid and at least one acidic amino acid, and a non-ionic detergent, e.g. polysorbate or poloxamer. The invention further relates to a method of producing such formulations, and a method of treatment using such formulations.

BACKGROUND OF THE INVENTION

The growth hormones from man and from the common domestic animals are proteins of approximately 191 amino acids, synthesized and secreted from the anterior lope of the pituitary gland. Human growth hormone consists of 191 amino acids.

Growth hormone is a key hormone involved in the regulation of not only somatic growth, but also in the regulation of metabolism of proteins, carbohydrates and lipids. The major effect of growth hormone is to promote growth.

The organ systems affected by growth hormone include the skeleton, connective tissue, muscles, and viscera such as liver, intestine, and kidneys.

Until the development of the recombinant technology and the cloning of the growth hormone gene now giving rise to production of e.g. human growth hormone (hGH) and Met-hGH in industrial scale, human growth hormone could only be obtained by extraction from the pituitary glands of human cadavers. The very limited supplies of growth hormone restricted the use thereof to longitudinal growth promotion in childhood and puberty for treatment of dwarfism, even though it has been proposed for inter alia treatment of short stature (due to growth hormone deficiency, normal short stature and Turner syndrome), growth hormone deficiency in adults, infertility, treatment of burns, wound healing, dystrophy, bone knitting, osteoporosis, diffuse gastric bleeding, and pseudoarthrosis.

Furthermore, growth hormone has been proposed for increasing the rate of growth of domestic animals or for decreasing the proportion of fat.

Pharmaceutical preparations of growth hormone tend to be unstable. Degradation products such as deamidated or sulfoxydated products and dimer or polymer forms are generated—especially in solutions of growth hormone.

The predominant chemical degradation reactions of hGH are 1) deamidation by direct hydrolysis or via a cyclic succinimide intermediate to form various amounts of L-asp-hGH, L-iso-asp-hGH, D-asp-hGH, and D-iso-asp-hGH (ref 1-3), 2) oxidation of the methionine residues in positions 14 and 125 (ref 4-9), and 3) cleavage of peptide bonds.

Deamidation especially takes place at the Asn in position 149.

hGH is rather easily oxidized in positions 14 and 125, especially in solution (4-8), since the oxidation of hGH in solution forming sulfoxides is normally due to the oxygen dissolved in the preparation.

At present, it is not believed that these degradation products should have toxic or altered biological activity or receptor binding properties, but there is indication to the effect that the conformation stability of the sulfoxides is reduced as compared to native hGH.

Other "degradation products" of growth hormone are aggregation products such as dimers and polymers. Studies have been performed to clarify the role of these forms in inducing an immune response with measurable amounts of antibodies to native hGH. These studies have indicated that aggregates of hGH are the primary cause of immunogenicity in patients.

Thus, it is desirable in a pharmaceutical formulation to avoid the formation of aggregates of growth hormone since such aggregates are capable of causing undesirable immunogenicity or altered half-life.

The kinetics of degradation depend on temperature, pH and various additives or adjuvants in the hGH formulation.

Due to the instability, a growth hormone formulation is at present normally lyophilized and stored in the lyophilized form at 2-8° C. until it is reconstituted for use in order to minimize the degradation. The lyophilized pharmaceutical preparations comprising hGH are reconstituted by the patient and then stored as a solution during the use for a period of up to 30 days, during which some degradation will take place.

It is at present preferred to reconstitute the growth hormone as late as possible before use and to store and ship the preparation in a lyophilized state. The chain from the manufacturer to the pharmacy is apt for handling the preparations at a controlled low temperature of e.g. 2-8° C. which allows for a shelf life of up to three years.

Preferably, a lyophilized and then reconstituted preparation should be stable with the end user in a lyophilized state for about one month and additionally for one month in a reconstituted state in a pen device for the intended period of use of a cartridge.

As an alternative to lyophilized and reconstituted preparations, growth hormone may be formulated as a liquid formulation suitable for use in vials or in a pen system for self-medication. The extended use of pen systems for self-medication and the expanded field of use calls for a preparation which is stable for a sufficient long time with the end user. Such stabilization is of very great importance when moving the administration of the growth hormone from clinics to the homes of the individuals to be treated where optimal storage conditions may not be available. A "ready to use" formulation furthermore diminishes any handling problems in connection with reconstitution and thus represents a convenience for the patient.

A stable dissolved preparation comprising growth hormone may be produced ready to use in the form of vials used by the patient in combination with conventional syringes or as cartridges fitting into the pen device used by the patient. In both cases, the patient may then avoid the reconstitution of the preparation and, hence, will not have to be in the possession of a lyophilized preparation, a suitable vehicle for reconstitution as well as the necessary skill and sterile equipment for sterile reconstitution of the preparation. Safety reasons also make it desirable to avoid the reconstitution of a lyophilized preparation just before the use of the preparation.

From the manufacturer's point of view, it may be an advantage to avoid the lyophilization step in the production of growth hormone preparations. Lyophilization is a time consuming and costly process and is also often a "bottleneck" in the production due to the limited capacity of the freeze drier.

Thus, there is a need for more stable dissolved preparations of growth hormone in order to facilitate the handling to be performed by the patient.

Thus, there is also a need to reduce the rate of the degradation processes in order to allow for dissolved hGH preparations being stable during shelf life and during the period of use of up to about one month.

PRIOR ART

Prior attempts to stabilize hGH has not fully succeeded in preventing the formation of dimer. The problems associated with dimer formation is e.g noted in Becker, G. W., *Biotechnology and Applied Biochemistry* 9, 478 (1987).

International Patent Publication No. WO 89/09614 and Australian patent application No. 30771/89 disclose a stable pharmaceutical formulation containing human growth hormone, glycine, and mannitol. Such a formulation shows improved stability during normal processing and storage in a lyophilized state as well as in the period of use after the reconstitution.

Published European patent application No. 303 746 discloses that animal growth hormone may be stabilized with various stabilizers to give decreased formation of insolubles and preservation of the soluble activity in aqueous environments, such stabilizers including certain polyols, amino acids, polymers of amino acids having a charged side group at physiological pH, and choline salts. Polyols are selected from the group consisting of non-reducing sugars, sugar alcohols, sugar acids, pentaerythritol, lactose, water-soluble dextrans and Ficoll; amino acids are selected from the group consisting of glycine, sarcosine, lysine or salts thereof, serine, arginine or salts thereof, betaine, N,N,-dimethyl-glycine, aspartic acid or salts thereof, glutamic acid or salts thereof, a polymer of an amino acid having a charged side group at physiological pH may be selected from polylysine, polyaspartic acid, polyglutamic acid, polyarginine, polyhistidine, polyornithine and salts thereof, and choline derivatives are selected from the group consisting of choline chloride, choline dihydrogen citrate, choline bitartrate, choline bicarbonate, tricholine citrate, choline ascorbate, choline borate, choline gluconate, choline phosphate, di(choline)sulphate and dicholine mucate.

U.S. Pat. No. 4,917,685 discloses a delivery device designed to be implanted comprising growth hormone stabilized using the same stabilizers as mentioned in EP 303746.

Published European patent application No. 374,120 discloses a stabilized formulation comprising hGH and a polyol having three hydroxy groups. Glycerol and tris(hydroxymethyl)aminomethane are mentioned. Furthermore, the presence of histidine hydrochloride as a buffer together with the polyol is disclosed.

International Patent Publication No. WO 93/12811 discloses stabilized formulations of growth hormone in the form of a lyophilized powder or an aqueous solution comprising asparagine.

International Patent Publication No. WO 93/12812 discloses stabilized formulations of growth hormone in the form of a lyophilized powder or an aqueous solution comprising histidine. In such formulations the deamidation is reduced by 25-30% as compared to a corresponding formulation of growth hormone comprising phosphate buffer.

International patent Publication No. WO 96/11703 discloses stabilized formulations of growth hormone comprising isoleucine.

International patent Publication No. WO 96/11702 discloses stabilized formulations of growth hormone comprising valine.

International patent Publication No. WO 96/11704 discloses stabilized formulations of growth hormone comprising leucine.

International Patent Publication No. WO 93/19776 discloses protein formulations comprising growth hormone comprising citrate as buffer substance being more stable than formulations comprising phosphate buffer. The formulations may also comprise amino acids such as glycine and alanine and/or mannitol or other sugar alcohols and/or glycerol and/or other carbohydrates and optionally a preservative such as benzyl alcohol.

International Patent Publication No. WO 94/03198 discloses a stable aqueous formulation containing human growth hormone, a buffer, a non-ionic surfactant, and, optionally, a neutral salt, mannitol, or, a preservative. The buffer may be histidine even though citrate is preferred. The application discloses a preferred formulation containing citrate as buffer, and natrium chloride and polysorbate 20 (Tween 20) for stabilization. This combination stabilizes the said aqueous formulation against aggregation but does give rise to a considerate amount of deamidated growth hormone.

International patent Publication No. WO 95/35116 discloses a stable lyophilized formulation containing saccharose and, optionally, mannitol.

DESCRIPTION OF THE INVENTION

It has now surprisingly been found that a pharmaceutical formulation comprising growth hormone, or a derivative of growth hormone, and an amino acid selected from the group of Asp, Ile, Val or Leu, histidine, or a derivative of histidine, or a peptide comprising at least one basic amino acid residue and at least one acidic amino acid residue, and a non-ionic detergent, wherein the amount of peptide, or Asp, Ile, Val, Leu or His, or derivative of histidine is from about 0.01 to about 10 mg per mg of GH shows a high stability against deamidation and aggregation. The stability of the product allows for the storing and shipment thereof in a lyophilized state or in the form of a dissolved or re-dissolved formulation.

The peptide comprising at least one basic amino acid residue and at least one acidic amino acid residue to be used in accordance with the present invention may be a peptide comprising up to 20 amino acid residues, preferably from 3 to 10 amino acid residues, more preferred from 3 to 6 amino acid residues such as 3 or 4 amino acid residues (e.g. Lys-Gly-Asp-Ser). In accordance with one aspect of the invention, the basic and acid amino residues of shorter peptides are separated by 1 or 2 amino acid residues. The peptides preferably comprise the naturally occurring alpha amino acid residues. The amino acid(s) may be l or d amino acid(s) or a mixture thereof. "Acidic amino acid residues" are e.g. Glu or Asp, and "basic amino acid residues" are e.g. Lys or Arg.

The derivatives of histidine to be used in accordance with the present invention may be amides and esters of histidine such as the methyl or ethyl ester, dipeptides having the sequence His-X or X-His, where X is a naturally occurring α-amino acid residue, and analogues or derivatives of His such as imidazole, des-amino-His or poly-His.

In a preferred aspect, the invention relates to a pharmaceutical formulation comprising growth hormone (GH) or a derivative of growth hormone and an amino acid selected from the group of Asp, Ile, Val or Leu, and a non-ionic detergent, wherein the amount of the amino acid selected from the group of Asp, Ile, Val or Leu is from about 0.01 to about 10 mg per mg of GH. In another preferred aspect, the invention relates to a pharmaceutical formulation comprising growth hormone (GH) or a derivative of growth hormone and histidine, or a derivative of histidine, or a peptide comprising at least one basic amino acid residue and at least one acidic amino acid residue, and a non-ionic detergent, wherein the amount of peptide or histidine or derivative of histidine is from about 0.01 to about 10 mg per mg of GH.

In a preferred embodiment of the above aspect, the amount of peptide, or selected amino acid, or histidine, or derivative of histidine, is from about 0.05 to about 5 mg per mg of GH, more preferred from about 0.05 to about 1 mg per mg of GH, even more preferred from about 0.05 to about 0.7 mg per mg of GH, and even more preferred from about 0.05 to about 0.5 mg per mg of GH.

In a preferred embodiment of the above aspect, the non-ionic detergent is selected from a polysorbate or a poloxamer, e.g. polysorbate 20, poloxamer 188, or poloxamer 407 (e.g. Pluronic® F68, Lutrol 127, Tween 20), most preferred poloxamer 188.

In another aspect, the invention relates to a pharmaceutical formulation of growth hormone, or a derivative of growth hormone, comprising an amino acid selected from the group of Asp, Ile, Val, Leu or His, or a derivative of histidine, or a peptide comprising at least one basic amino acid residue and at least one acidic amino acid residue, and a non-ionic detergent, wherein the amount of non-ionic detergent is from about 0.01 to about 10 mg per mg of GH.

In a preferred aspect, the invention relates to a pharmaceutical formulation comprising growth hormone (GH) or a derivative of growth hormone, and an amino acid selected from the group of Asp, Ile, Val or Leu, and a non-ionic detergent, wherein the amount of non-ionic detergent is from about 0.01 to about 10 mg per mg of GH. In another preferred aspect, the invention relates to a pharmaceutical formulation comprising growth hormone (GH), or a derivative of growth hormone, and histidine, or a derivative of histidine, or a peptide comprising at least one basic amino acid residue and at least one acidic amino acid residue, and a non-ionic detergent, wherein the amount of non-ionic detergent is from about 0.01 to about 10 mg per mg of GH.

In a preferred embodiment of the above aspect, the amount of non-ionic detergent is from about 0.01 to about 10 mg per mg of GH, more preferred from about 0.05 to about 5 mg per mg of GH, even more preferred from about 0.1 to about 3 mg per mg of GH, even more preferred from about 0.1 to about 2 mg per mg of GH.

In a preferred embodiment of the above aspect, the non-ionic detergent is selected from a polysorbate or a poloxamer, e.g. polysorbate 20, poloxamer 188, or poloxamer 407 (e.g. Pluronic® F68, Lutrol 127, Tween 20), most preferred poloxamer 188.

Another aspect of the invention is a pharmaceutical formulation comprising growth hormone, or a derivative of growth hormone, and an amino acid selected from the group of Asp, Ile, Val, Leu or His, or a derivative of histidine, or a peptide comprising at least one basic amino acid and at least one acidic amino acid, and a non-ionic detergent, wherein the amount of peptide, or Asp, Ile, Val, Leu or His, or derivative of histidine, is from about 0.01 to about 10 mg per mg of GH, and the amount of non-ionic detergent is from about 0.1 to about 2 mg per mg of GH.

In a preferred aspect, the invention relates to a pharmaceutical formulation comprising growth hormone or a derivative of growth hormone, and an amino acid selected from the group of Asp, Ile, Val or Leu, and a non-ionic detergent, wherein the amount of Asp, Ile, Val or Leu is from about 0.01 to about 10 mg per mg of GH, and the amount of non-ionic detergent is from about 0.1 to about 2 mg per mg of GH. In another preferred aspect, the invention relates to a pharmaceutical formulation comprising growth hormone, or a derivative of growth hormone, and histidine, or a derivative of histidine, or a peptide comprising at least one basic amino acid residue and at least one acidic amino acid residue, and a non-ionic detergent, wherein the amount of peptide or histidine or derivative of histidine is from about 0.01 to about 10 mg per mg of GH, and the amount of non-ionic detergent is from about 0.1 to about 2 mg per mg of GH.

In a preferred embodiment of the above aspect, the amount of peptide, or Asp, Ile, Val, Leu or His, or derivative of histidine, is from about 0.05 to about 5 mg per mg of GH, more preferred from about 0.05 to about 1 mg per mg of GH, even more preferred from about 0.05 to about 0.7 mg per mg of GH, and even more preferred from about 0.05 to about 0.5 mg per mg of GH.

In a preferred embodiment of the above aspect, the non-ionic detergent is selected from a polysorbate or a poloxamer, e.g. polysorbate 20, poloxamer 188, or poloxamer 407 (e.g. Pluronic® F68, Lutrol 127, Tween 20), most preferred poloxamer 188.

Another aspect of the invention relates to a pharmaceutical formulation comprising growth hormone, or an amino acid selected from the group of Asp, Ile, Val, Leu or His, or a derivative of histidine, or a peptide comprising at least one basic amino acid residue and at least one acidic amino acid residue, and a poloxamer.

In a preferred aspect, the invention relates to pharmaceutical formulation comprising growth hormone (GH) or a derivative of growth hormone, and an amino acid selected from the group of Asp, Ile, Val or Leu, and a poloxamer. In another preferred aspect, the invention relates to a pharmaceutical formulation comprising growth hormone, or a derivative of growth hormone, and histidine, or a derivative of histidine, or a peptide comprising at least one basic amino acid residue and at least one acidic amino acid residue, and a poloxamer.

In a preferred embodiment of the above aspect, the poloxamer is selected from poloxamer 188, or poloxamer 407, most preferred poloxamer 188 (e.g. Pluronic® F68). In another preferred embodiment, the formulation comprises histidine, or a derivative of histidine. In a preferred embodiment, the amount of peptide, or Asp, Ile, Val, Leu or His, or derivative of histidine is from about 0.05 to about 5 mg per mg of GH, more preferred from about 0.05 to about 1 mg per mg of GH, even more preferred from about 0.05 to about 0.7 mg per mg of GH, and even more preferred from about 0.05 to about 0.5 mg per mg of GH. In a preferred embodiment, the amount of non-ionic detergent is from about 0.05 to about 5 mg per mg of GH, more preferred from about 0.1 mg to about 3 mg per mg of GH, more preferred from about 0.1 to about 2 mg per mg of GH The formulation of the invention may be in the form of a lyophilized powder to be reconstituted later using conventional vehicles such as distilled water, or water for injection, or it may be in the form of an aqueous solution comprising growth hormone. Such vehicles may comprise conventional preservatives such as m-cresol, phenol, and benzyl alcohol. As bulking agent(s) for lyophilization, one or more of the members from the group consisting of sugar alcohols, e.g. mannitol, and disaccharides, e.g. sucrose, may be selected.

Lyophilized preparations comprising sucrose are preferred due to a very high stability, and preparations comprising sucrose and mannitol are especially preferred combining very high stability with a very good processability giving firm lyophilized products being readily dissolvable and very stable in solution for an extended period of time after dissolution. Further preferred preparations according to the invention are preparations comprising mannitol and sucrose or trehalose as bulking agent for the lyophilization. Preparations according to the invention comprising mannitol and a disaccharide normally comprises about equal amount of the two constituents on a weight basis.

The amount of sucrose present in the preparations of the invention may vary within wide limits. The ratio of growth hormone to sucrose may vary from 0.005 to 1.5 on a weight basis. Thus, the amount of sucrose may be from 0.67 to 200 mg per mg of growth hormone, an amount of from 1.1 to 50 mg per mg of growth hormone being preferred.

In a preferred embodiment of the invention, the growth hormone is human growth hormone (hGH) and the pharmaceutical composition is further comprising a carrier in the form of an aqueous buffer. Such an aqueous preparation is in a ready-to-use form and may be stored and shipped as such without any considerable degradation.

A buffer to be used in a solution of growth hormone may e.g. be histidine, citrate, tartrate, or phosphate buffer. L-histidine has a pKA of 6.0 and is, accordingly, suitable as a buffer itself in an interval of pH from about 5 to about 7.

In a further aspect, the invention relates to a method of preparing a pharmaceutical formulation comprising a growth hormone, or a derivative of growth hormone, and an amino acid selected from the group of Asp, Ile, Val, Leu or His, or a derivative of histidine or a peptide comprising at least one basic amino acid residue and at least one acidic amino acid residue, and a non-ionic detergent, wherein the appropriate amount of growth hormone, or derivative of growth hormone, is dissolved in a solution comprising an amino acid selected from the group of Asp, Ile, Val, Leu or His, or a derivative of histidine, or a peptide comprising at least one basic amino acid residue and at least one acidic amino acid residue in deionized water, and a non-ionic detergent, e.g. a polysorbate or a poloxamer, optionally containing a preservative, and optionally containing an agent for adjusting the tonicity, and optionally adjusting the pH to a value from about 6.0 to about 8.8; the appropriate amount of GH being what makes the amount of peptide, Asp, Ile, Val, Leu or His, or derivative of histidine range from about 0.01 to about 10 mg per mg of GH.

In a further aspect, the invention relates to a method of preparing a pharmaceutical formulation comprising a growth hormone, or a derivative of growth hormone, and, an amino acid selected from the group of Asp, Ile, Val, Leu or His, or a derivative of histidine or a peptide comprising at least one basic amino acid residue and at least one acidic amino acid residue, and a non-ionic detergent, wherein the growth hormone, or derivative of growth hormone, is dissolved in a solution comprising an amino acid selected from the group of Asp, Ile, Val, Leu or His, or a derivative of histidine or a peptide comprising at least one basic amino acid residue and at least one acidic amino acid residue in deionized water, and a appropriate amount of non-ionic detergent, e.g. a polysorbate or a poloxamer, optionally containing a preservative, and optionally containing an agent for adjusting the tonicity, and optionally adjusting the pH to a value from about 6.0 to about 8.8; the appropriate amount of non-ionic detergent being what makes the amount of non-ionic detergent range from about 0.01 to about 10 mg per mg of GH.

In a further aspect, the invention relates to a method of preparing a pharmaceutical formulation comprising a growth hormone, or a derivative of growth hormone, and an amino acid selected from the group of Asp, Ile, Val, Leu or His, or a derivative of histidine, or a peptide comprising at least one basic amino acid residue and at least one acidic amino acid residue, and a non-ionic detergent, comprising dissolving such an amount of growth hormone, or derivative of growth hormone, that makes the amount of peptide, or Asp, Ile, Val, Leu or His, or derivative of histidine range from about 0.05 to about 0.5 mg per mg GH, in a solution comprising an amino acid selected from the group of Asp, Ile, Val, Leu or His, or a derivative of histidine, or a peptide comprising at least one basic amino acid residue and at least one acidic amino acid residue, and such an amount of a non-ionic detergent, e.g. a polysorbate or a poloxamer, that the amount of non-ionic detergent is from about 0.1 to about 2 mg per mg of GH, in deionized water, optionally containing a preservative, and optionally containing an agent for adjusting the tonicity, and optionally adjusting the pH to a value from about 6.0 to about 8.8.

In a further aspect, the invention relates to a method of preparing a pharmaceutical formulation comprising a growth hormone, or a derivative of growth hormone, and an amino acid selected from the group of Asp, Ile, Val, Leu or His, or a derivative of histidine, or a peptide comprising at least one basic amino acid residue and at least one acidic amino acid residue, and a poloxamer, wherein the growth hormone, or derivative of growth hormone, is dissolved in a solution comprising an amino acid selected from the group of Asp, Ile, Val, Leu or His, or a derivative of histidine, or a peptide comprising at least one basic amino acid residue and at least one acidic amino acid residue in deionized water, and a poloxamer, optionally containing a preservative, and optionally containing an agent for adjusting the tonicity, and optionally adjusting the pH to a value from about 6.0 to about 8.8.

The concentration of the amino acid selected from the group of Asp, Ile, Val, Leu or His, or a derivative of histidine, or a peptide comprising at least one basic amino acid and at least on acidic amino acid is preferably from about 1 mM to about 100 mM. More preferred, the concentration of Asp, Ile, Val, Leu, or His, or derivative of histidine, or peptide comprising at least one basic amino acid and at least on acidic amino acid is from about 2 mM to about 20 mM, most preferred from about 5 mM to about 15 mM.

The pharmaceutical formulations of the invention may be formulated for administration in any suitable way, e.g. by parenteral or oral administration or administration to a mucosal membrane, e.g. nasal administration. The pharmaceutical formulation may be presented in the form of a dose comprised in a vial or cartridge or any other suitable container such as a prefilled syringe or a pen device.

The pharmaceutical preparation of the invention may furthermore comprise salts conventionally used in order to facilitate the processing thereof, e.g. the lyophilization or reconstitution.

For stability reasons the pH of the solution is preferably adjusted to a value in the interval from about 6.0 to about 8.8, preferably from about 6.0 to about 7.0, more preferred from about 6.0 to about 6.8, even more preferred from about 6.0 to 6.3, and most preferred from about 6.0 to 6.2 (e.g. about 6.1).

The pH may be adjusted by adding an acid which has no adverse effect on the growth hormone, preferably a physiologically acceptable acid e.g. a mineral acid such as hydrochloric acid, sulphuric acid or nitric acid or an organic acid such as acetic acid or citric acid.

The pharmaceutical formulation of the invention may furthermore comprise salts for adjusting the tonicity and optionally an excipient in order to facilitate the processing thereof, e.g. lyophilization and the rapid and complete dissolution of a lyophilized formulation when reconstituting the formulation before use.

Such salts may be selected from conventional additives such as alkaline metal, alkaline earth metal or ammonium salts of organic acids such as citric acid, tartaric acid or acetic acid, e.g. sodium citrate, sodium tartrate or sodium acetate, or of mineral acids such as hydrochloric acid, e.g. sodium chloride.

An excipient may be selected from disaccharides such as lactose, trehalose, and sucrose, sugar alcohols such as mannitol, xylitol, erythritol, threitol, sorbitol or glycerol, polysaccharides such as the polymers commercialized as Dextran® products such as Dextran® 40, Dextran® 70 or Dextran® 75, and Ficoll® and polyvalent alcohols such as polyethylene glycol or polyvinyl alcohol or a combination of two or more of these.

In the present context "growth hormone" or "GH" may be growth hormone from any origin such as avian, bovine, equine, human, ovine, porcine, salmon, trout or tuna growth hormone, preferably bovine, human or porcine growth hormone, human growth hormone being most preferred. The growth hormone used in accordance with the invention may be native growth hormone isolated from a natural source, e.g. by extracting pituitary glands in a conventional manner, or a growth hormone produced by recombinant techniques, e.g as described in E. B. Jensen and S. Carlsen in Biotech and Bioeng. 36, 1-11 (1990). The "growth hormone derivative" may be a truncated form of growth hormone wherein one or more amino acid residues has (have) been deleted; an analogue thereof wherein one or more amino acid residues in the native molecule has (have) been substituted by another amino acid residue, preferably the residue of a naturally occurring amino acid, as long as the substitution does not have any adverse effect such as antigenicity or reduced action; or a derivative thereof, e.g deamidated or sulfoxidated forms of the growth hormone or forms having an N- or C-terminal extension such as Met-hGH, Met-Glu-Ala-Glu-hGH or Ala-Glu-hGH. The preferred growth hormone is hGH. The growth hormone may be a concentrate obtained directly from the fermentation broth or a conventional lyophilized preparation which is dissolved in an appropriate solvent.

The term "derivatives of histidine" is used, for the present purpose, to designate amides and esters of histidine such as the methyl or ethyl ester, dipeptides such as His-Gly, His-Ala, His-Leu, His-Lys, His-Ser, His-Phe, and dipeptides such as Ala-His, Gly-His, Val-His, Glu-His, Met-His, Arg-His, Asp-His, Leu-His, Ser-His, and analogues or derivatives of His such as imidazole, des-amino-His or poly-His.

In the present context "non-ionic detergent" or "non-ionic surfactant" may be polysorbates, such as polysorbate 20 or 80, etc., and the poloxamers, such as poloxamer 188 or 407, Pluronic® polyols, and other ethylene/polypropylene polymers, etc. Amounts effective to provide a stable, aqueous formulation will be used, usually in the range of from about 0.01 to about 10 mg detergent per mg of growth hormone, preferably from about 0.05 to about 5 mg detergent per mg of growth hormone, more preferred from about 0.1 to about 2 mg detergent per mg of growth hormone.

The use of non-ionic detergents permits the formulation to be exposed to shear and surface stresses without causing denaturation of the protein.

The amount of non-ionic detergent in the formulations may be in the range of from 0.01 to about 10 mg detergent per mg of growth hormone, preferably from 0.05 to about 5 mg detergent per mg of growth hormone, most preferred from 0.1 to about 2 mg detergent per mg of growth hormone.

In the present context "disaccharide" is used to designate naturally occurring disaccharides such as sucrose, trehalose, maltose, lactose, sepharose, turanose, laminaribiose, isomaltose, gentiobiose or melibiose.

A peptide comprising at least one basic amino acid residue and at least one acidic amino acid residue to be used in accordance with the present invention is preferably comprising the naturally occurring α-amino acid residues. The amino acid(s) may be l or d amino acid(s) or a mixture thereof. A preferred peptide comprising at least one basic amino acid residue and at least one acidic amino acid residue is Lys-Gly-Asp-Ser.

In the present context "acidic amino acid residues" are e.g. Glu or Asp, and "basic amino acid residues" are e.g. Lys or Arg.

The solvent used in the method of the invention may be water, alcohols such as ethyl, n-propyl or isopropyl, butyl alcohol or mixtures thereof. To retard microbial growth, the solvent may comprise a preservative such as m-cresol, phenol, or benzyl alcohol.

The term "dose" of growth hormone refers to that amount that provides therapeutic effect in an administration regimen. The formulations hereof are prepared containing amounts of hGH at least about 0.1 mg/ml, preferably upwards of about 1 mg/ml, preferably from about 1 mg/ml to about 40 mg/ml, more preferably from about 1 mg/ml to about 25 mg/ml, more preferably from about 1 mg/ml to about 15 mg/ml e.g. from 1 mg/ml to about 10 mg/ml, calculated on the ready-to-use formulation. For use of these compositions in administration to human beings suffering from hypopituitary dwarfism, for example, these formulations contain from about 0.1 mg/ml to about 10 mg/ml, corresponding to the currently contemplated dosage regimen for the intended treatment. The concentration range is not critical to the invention and may be varied by the physician supervising the administration.

Another aspect of the invention relates to a method of treating a patient affectable by growth hormone comprising treating the patient with an amount of the pharmaceutical formulation according to the invention effective to treat said disorder.

The invention is explained more in detail in the below Examples which illustrate the invention. They are not to be considered as limiting the scope of the invention being defined by the appended claims.

EXPERIMENTAL PART

Example 1

Inhibition of Aggregation

Liquid formulations of hGH was prepared by dissolving hGH in a solution of excipients and adjusting the pH with HCl/NaOH. The composition of the formulations were:

| | |
|---|---|
| hGH | 5 mg/ml |
| Mannitol | 45 mg/ml |
| L-histidin | 0.62 mg/ml |
| Phenol | 2.5 mg/ml |
| Surfactant | x mg/ml | pH = y (from 6.1 to 6.8)

The appearance of the solutions was examined visually after the solutions had been stored 1 day at 8° C. and rotated for 19 hour (20 rpm) at 25° C., respectively:

| Surfactant | x (mg/ml) | pH (y) | Appearance after 1 day at 8° C. | Appearance after |
|---|---|---|---|---|
| 19 hours rotation- | 0 | 6.1 | Precipitation | Precipitation |
| — | 0 | 6.3 | Precipitation | Many flakes |
| — | 0 | 6.5 | Flakes | Many flakes |
| — | 0 | 6.8 | Flakes | Some flakes |
| Pluronic L64 | 0.5 | 6.8 | Clear, few flakes | Many small flakes |
| Pluronic L64 | 1 | 6.8 | Clear, few flakes | Clear, some flakes |
| Pluronic F68 | 2 | 6.1 | Clear | Clear, some flakes |
| Pluronic F68 | 2 | 6.3 | Clear | Clear, few flakes |
| Pluronic F68 | 2 | 6.5 | Clear | Clear, few flakes |
| Pluronic F68 | 2 | 6.8 | Clear | Clear, some flakes |
| Lutrol F127 | 1 | 6.1 | Clear | Clear, some flakes |
| Lutrol F127 | 1 | 6.3 | Clear | Clear, some flakes |
| Lutrol F127 | 1 | 6.5 | Clear | Clear, few flakes |
| Lutrol F127 | 1 | 6.8 | Clear | Not analysed |
| Tween 20 | 2 | 6.1 | Slight precipitation | Reasonably clear, some flakes |
| Tween 20 | 2 | 6.3 | Clear | Clear, some flakes |
| Tween 20 | 2 | 6.5 | Clear, some flakes | Clear, few flakes |
| Tween 20 | 2 | 6.8 | Clear | Clear, some flakes |

Example 2

Rate of Deamidation

The eight formulations tabulated below were prepared by adding the hGH to a solution containing the excipients. pH was adjusted to 6.1. The preparations were then placed for 28 days at 25° C. and for 14 days at 37° C. and analysed for formation of deamidated forms of hGH. Rate constants for the deamidation were calculated on basis of the stability data. In the table below the contents of hGH and excipients are given in mg/ml and the rate constants $k_{25° C.}$ and $k_{37° C.}$ are given in days$^{-1}$

| hGH | Phenol | Pluronic F68 | Lutrol F127 | L-histidin | Di-sodium hydrogen citrate | Mannitol | NaCl | $k_{25°C.}$ | $k_{37°C.}$ |
|---|---|---|---|---|---|---|---|---|---|
| 5 | 2.5 | 2 | | 0.62 | | 45 | | 0.00180 | 0.00860 |
| 6.7 | 2.5 | 2 | | | 2.2 | 45 | | 0.00221 | 0.0127 |
| 6.7 | 2.5 | 2 | | 0.62 | | | 5.8 | 0.00244 | 0.0110 |
| 6.7 | 2.5 | 2 | | | 2.2 | | 5.8 | 0.00263 | 0.0143 |
| 5 | 2.5 | | 1 | 0.62 | | 45 | | 0.00178 | 0.00914 |
| 6.7 | 2.5 | | 1 | | 2.2 | 45 | | 0.00221 | 0.0128 |
| 6.7 | 2.5 | | 1 | 0.62 | | | 5.8 | 0.00236 | 0.0112 |
| 6.7 | 2.5 | | 1 | | 2.2 | | 5.8 | 0.00259 | |
| 0.0139 | | | | | | | | | |

Example 3

Formation of Deamidated Forms

The formulations tabulated below were prepared by adding the hGH to a solution containing the excipients and adjusting the pH. The preparations were then placed for 3 months at 8° C. and 25° C. and analysed for formation of deamidated forms of hGH.

| hGH (mg/ml) | Surfactant[1] (mg/ml) | Phenol (mg/ml) | L-histidin (mg/ml) | Mannitol (mg/ml) | pH | t = 0 | Content of desamido forms (%) 3 months at 8° C. | 12 weeks at 25° C. | 3 weeks at 37° C. |
|---|---|---|---|---|---|---|---|---|---|
| 6.25 | 2 (F68) | 2.5 | 0.62 | 45 | 6.3 | 0.6 | 2.7 | 18.1 | 21.1 |
| 6.25 | 2 (F68) | 2.5 | 0.62 | 45 | 6.2 | 0.5 | 2.5 | 16.2 | 18.7 |
| 6.25 | 2 (F68) | 2.5 | 0.62 | 45 | 6.1 | 0.6 | 2.2 | 14.8 | 17.1 |
| 3.33 | 3 (F68) | 3.0 | 0.68 | 40 | 6.1 | 1.3 | 3.0 | 15.5 | n.a. |
| 6.67 | 3 (F68) | 3.0 | 0.68 | 40 | 6.1 | 1.0 | 3.2 | 16.6 | n.a. |
| 10.0 | 3 (F68) | 3.0 | 1.1 | 39 | 6.1 | 0.6 | 3.8 | 16.7 | n.a. |
| 6.25 | 1 (L127) | 2.5 | 0.62 | 45 | 6.1 | 0.6 | 2.5 | 15.4 | 18.2 |
| 6.25 | 2 (T20) | 2.5 | 0.62 | 45 | 6.1 | 0.6 | n.a. | n.a. | 16.6 |

[1]Type of surfactant is given in parantheses: F68 = Pluronic F68 = poloxamer 188 F127 = Lutrol 127 = poloxamer 407 T20 = Tween 20 = polysorbate 20

Example 4

24 Formulations were Prepared from the Below Formula hGH 3.33 to 13.1 mg/ml

L-histidin 0.78 mg/ml

Mannitol 22 mg/ml

Sucrose 21 mg/ml

Poloxamer 188 1.33-5.33 mg/ml

Preservative: Benzylalcohol (0-20 mg/ml) or Phenol (0-5 mg/ml)

The formulations were prepared by adding the hGH to a solution of the excipients. pH was adjusted to 6.8. The formulations were kept at 25° C. for 4 weeks and then the clarity of the solutions were measured as the absorbance at 340 nm. The absorbance at 340 nm indicate the degree of aggregation in the solutions.

| hGH (mg/ml) | Poloxamer 188 (mg/ml) | Benzylalcohol (mg/ml) | | | | Phenol (mg/ml) | |
|---|---|---|---|---|---|---|---|
| | | 0 | 15 | 18 | 20 | 2.5 | 5 |
| 3.33 | 1.33 | 0.009 | 0.019 | 0.045 | 0.016 | 0.015 | 0.020 |
| 6.67 | 2.66 | 0.046 | 0.022 | 0.041 | 1) | 0.025 | 0.026 |
| 10.0 | 4.0 | 0.022 | 0.060 | 1) | 1) | 0.034 | 0.050 |
| 13.1 | 5.33 | 0.018 | 0.041 | 0.042 | 1) | 0.054 | 0.071 |

1): dissolution of hGH not possible.

REFERENCES

1) Y.-C. J. Wang and M. A. Hanson. Parenteral Formulations of Proteins and Peptides: Stability and Stabilizers. J. Parenteral Science and Technology 42 (Suppl.) (1988) 53-525.
2) M. C. Manning, K. Patel, R. T. Borchardt. Stability of Protein Pharmaceuticals. Pharmaceutical Research 6 (11) (1989) 903-918.
3) B. A. Johnson, J. M. Shirokawa, W. S. Hancock, M. W. Spellman, L. J. Basa and D. W. Asward. J. Biol. Chem. 264, 1462-71 (1989).
4) L. C. Teh et al., J. Biol. Chem., 262, 785-794 (1987).
5) G. W. Becker et al., Biotech. Appl. Biochem., 10, 326-337 (1988).
6) R. A. Houghten et al., Arch. Biochem. Biophys., 178, 350-355 (1977).
7) R. M. Riggin et al., Anal. Biochem., 167, 199-209 (1987).
8) P. Gellerfors et al., Acta Paediatr. Scand (suppl), 370, 93-100 (1990).
9) M. J. Kaufman, Pharm. Res., 7 (3) 289-292 (1990).

The invention claimed is:

1. An aqueous pharmaceutical formulation comprising a) about 1 mg/ml to about 15 mg/ml of human growth hormone (hGH), b) histidine in an amount of about 0.05-about 0.5 mg per mg hGH, c) Poloxamer 188 in an amount of about 0.1-about 2 mg per mg hGH, d) mannitol in an isotonicity conferring amount, and e) phenol in an amount that confers a preservative effect, wherein the formulation has a pH 6.0-6.2, and wherein the hGH is dissolved in said formulation.

2. The formulation of claim 1, wherein the formulation has a pH of about 6.1.

\* \* \* \* \*

UNITED STATES PATENT AND TRADEMARK OFFICE
CERTIFICATE OF CORRECTION

PATENT NO. : 8,841,252 B2
APPLICATION NO. : 12/575886
DATED : September 23, 2014
INVENTOR(S) : Soeren Bjoern et al.

It is certified that error appears in the above-identified patent and that said Letters Patent is hereby corrected as shown below:

In the Claims:

At column 14, claim 1, beginning at line number 23, please amend the line as follows:

"...about 1 mg/ml to about 15 mg/ml of human growth hormone..."

At column 14, claim 1, beginning at line number 28, please amend the line as follows:

"...preservative effect, wherein the formulation has a pH pf about 6.0-6.2,"

Signed and Sealed this
Twenty-first Day of April, 2015

Michelle K. Lee
*Director of the United States Patent and Trademark Office*